US011350826B2

(12) United States Patent
Secco et al.

(10) Patent No.: US 11,350,826 B2
(45) Date of Patent: Jun. 7, 2022

(54) DEVICE AND METHOD FOR ACQUISITION OF MEDICAL IMAGES FOR THE ANALYSIS OF ULCERS

(71) Applicant: POLITECNICO DI TORINO, Turin (IT)

(72) Inventors: Jacopo Secco, Turin (IT); Orlando Selenu, Lotzorai (IT); Marco Farina, Turin (IT)

(73) Assignee: Politecnico Di Torino, Turin (IT)

( * ) Notice: Subject to any disclaimer, the term of this patent is extended or adjusted under 35 U.S.C. 154(b) by 565 days.

(21) Appl. No.: 16/061,601

(22) PCT Filed: Dec. 21, 2016

(86) PCT No.: PCT/IB2016/057868
§ 371 (c)(1),
(2) Date: Jun. 12, 2018

(87) PCT Pub. No.: WO2017/109719
PCT Pub. Date: Jun. 29, 2017

(65) Prior Publication Data
US 2018/0368693 A1     Dec. 27, 2018

(30) Foreign Application Priority Data

Dec. 23, 2015 (IT) .................... IT102015000087450

(51) Int. Cl.
*A61B 5/00* (2006.01)
*A61B 5/107* (2006.01)

(52) U.S. Cl.
CPC .......... *A61B 5/0077* (2013.01); *A61B 5/0059* (2013.01); *A61B 5/0082* (2013.01);
(Continued)

(58) Field of Classification Search
None
See application file for complete search history.

(56) References Cited

U.S. PATENT DOCUMENTS 4,758,730 A * 7/1988 Bazin .................. A61B 5/0059
250/559.16
2005/0241652 A1* 11/2005 Hanin .................... A61Q 19/08
128/898
(Continued)

FOREIGN PATENT DOCUMENTS

CN         1971619 A      5/2007
JP      2006-271840 A    10/2006
(Continued)

OTHER PUBLICATIONS

Japanese Office Action dated Oct. 1, 2020, issued in Japanese Application No. 2018-528970.
(Continued)

*Primary Examiner* — Pascal M Bui Pho
*Assistant Examiner* — Farouk A Bruce
(74) *Attorney, Agent, or Firm* — Workman Nydegger

(57) ABSTRACT

A device for acquisition of medical images of an ulcer includes a plurality of light sources arranged on the perimeter of a closed regular plane geometry, and adapted to illuminate an ulcer by respective light beams covering the surface of the wound in an overlapped fashion; an image acquisition device placed within the perimeter of the light sources and adapted to acquire medical images of said illuminated ulcer.

13 Claims, 5 Drawing Sheets

(52) U.S. Cl.
CPC .......... *A61B 5/1079* (2013.01); *A61B 5/6844* (2013.01); *A61B 5/746* (2013.01)

(56) References Cited

U.S. PATENT DOCUMENTS

| | | | | |
|---|---|---|---|---|
| 2006/0126929 A1* | 6/2006 | Kim | ..................... | G01B 11/254 |
| | | | | 382/154 |
| 2008/0260221 A1* | 10/2008 | Unal | ....................... | G06T 7/149 |
| | | | | 382/128 |
| 2011/0304705 A1 | 12/2011 | Kantor et al. | | |
| 2013/0053701 A1* | 2/2013 | Wiest | ..................... | A61B 5/445 |
| | | | | 600/476 |

FOREIGN PATENT DOCUMENTS

| | | |
|---|---|---|
| JP | 2015-228927 A | 12/2015 |
| WO | 2014/184274 A1 | 11/2014 |

OTHER PUBLICATIONS

International Search Report and Written Opinion dated Apr. 3, 2017, issued in PCT Application No. PCT/IB2016/057868, filed Dec. 21, 2016.
International Preliminary Report on Patentability dated Jun. 26, 2018, issued in PCT Application No. PCT/IB2016/057868, filed Dec. 21, 2016.

\* cited by examiner

DEVICE AND METHOD FOR ACQUISITION OF MEDICAL IMAGES FOR THE ANALYSIS OF ULCERS

BACKGROUND OF THE INVENTION

1. The Field of the Invention

The present invention relates to the acquisition of medical images of ulcers.

More specifically, the present invention relates to a device for acquiring and processing medical images of ulcers and to a method for acquisition of medical images of ulcers.

2. The Relevant Technology

The term "cutaneous ulcer" refers to a lesion that shows itself in a topical region of the body and in the underlying tissues, which is due to absent or poor supply of blood in that region. Differently from a common wound, an ulcer has limited or slower capability of healing because of the insufficient blood volume supplied in the area involved.

Ulcers can be caused by several irritative or pathological factors, such as, for example, diabetes, continuous and protracted pressure on a particular body region (decubitus ulcers), or lesions or malfunctions in the vascular district (venous or arterial ulcers).

In addition to the above, sociological and statistical analyses have shown that, depending on the level of development of the country taken into account and on the condition of the local health system and structures, a percentage ranging from 1.2% to 18% of the overall population suffers from or is affected by cutaneous ulcers.

By way of example, the U.S. health system alone incurs a yearly cost of 3.5 to 7 billion dollars for treating cutaneous ulcers.

At present, cutaneous ulcers are treated through continual and periodic specialist medications. During the examination, the doctor removes the previous bandage, visually evaluates the wound and, according to the circumstances, renews the dressing. In order to evaluate the wound, it is necessary to take into consideration three essential parameters and their variations over time (with reference to the previous examinations).

The main characteristics that denote the healing or worsening of the lesion are the following: extension, depth and colour of the wound. By correlating the three variables and comparing them with the previous conditions, the specialist can apply the best medication, decide if the ulcer is necrotic (which in most cases will require surgical removal of the tissue part or, at worst, of the whole limb), and possibly prescribe an integrative pharmacological treatment.

Notwithstanding its confirmed curative effectiveness, this sequence of steps involves much discomfort for the patients, who are compelled to move in order to reach the place of treatment despite the suffered pain and the various problems that normally arise in such circumstances.

It has been statistically proven that more than 60% of the people affected by this kind of disorder are more than 65 years old, and 90% of these people have severe walking problems. Sometimes some movements are potentially useless, since the doctor, after having evaluated the condition of the ulcer, cannot apply a new type of medication yet.

In general, however, the most common medications can be applied by those who take care of the patient daily at home, after they have been properly instructed by the specialist.

Therefore, a need is felt for avoiding useless and detrimental patients' trips to the places of treatment of their ulcers unless strictly necessary. Moreover, given the number of patients and the number of examinations required for each patient (usually for a time of at least 2-3 months), it is difficult for the specialist to conduct an examination correctly in a short time.

In an attempt to solve the above-mentioned problems, the following devices have been created:

Mavis™: a stereolithographic device which, by projecting parallel luminous strips in the region of the wound, calculates the colour and three-dimensional geometry thereof. Mavis is a big, non-transportable device that cannot automatically detect and recognize a wound; in fact, the ulcer must be highlighted manually on the images by the doctor;

Digiskin™: a device that requires the use of a digital camera and an optical raster to highlight the granulation patterns (variations in the pathological tissue of a wound). It can manually detect the wound a posteriori;

ATOS™ and ATOS II™: stereophotographic methods for analysis of cutaneous ulcers, which utilize two cameras for reconstructing a three-dimensional image of the wound. The image thus obtained is then analyzed by manually selecting a posteriori the area of the lesion;

Aranz Silhouette™: a device that uses a laser scanner to acquire an image of the wound; the lesion can then be detected and its diagnostic parameters can be calculated after manual detection a posteriori.

The above-mentioned devices can only be used by a doctor, in that they all lack automatic wound detection.

Moreover, as specified in the publication by de Franciscis, S., et al. "*A new photographic computerized measurement system for chronic wound assessment*", Acta Phlebol 15 (2014), 13-8, the above-described methods suffer from high variability of the light that illuminates the wound at the time of data acquisition.

SUMMARY OF THE INVENTION

It is therefore an object of the present invention to propose a device and a method for acquisition of medical images of ulcers, through which it is possible to automatically and accurately detect a patient's ulcers and evaluate their morphological characteristics, while also reducing the number of times that the patient is required to go to the place of treatment, this being only necessary when the doctor must directly treat the ulcer.

Some embodiments of the present invention relate to a device and a method for acquiring and processing medical images of ulcers which overcome the drawbacks of the prior art.

In one embodiment of the invention, the device for acquisition of medical images of an ulcer comprises a plurality of light sources arranged on the perimeter of a closed regular plane geometry, and adapted to illuminate an ulcer by means of respective light beams covering the surface of the wound in an overlapped fashion in order to outline a shadow area generated by a difference in level existing between a skin profile and the inside of the ulcer; image acquisition means placed within the perimeter of the light sources and adapted to acquire medical images of said illuminated ulcer, detecting both the illuminated parts and the shadow areas.

In another embodiment, the device further comprises a processing unit connected to the sources and to the image acquisition means, and adapted to control both the illumination of the ulcer and the acquisition of the images.

In another embodiment of the invention, the device further comprises a distance sensing device adapted to measure the distance between the device and the ulcer and to send an alarm signal if said distance exceeds a predefined threshold value.

In another embodiment of the invention, the distance sensing device is either analog or digital, acoustic or optical.

In another embodiment of the invention, the light sources are at least three.

In another embodiment of the invention, the light sources are white LEDs.

In another embodiment of the invention, the device further comprises removable memory means adapted to store the images acquired by the image acquisition means.

In another embodiment of the invention, the plane geometry has a minor axis of at least 10 cm.

In another embodiment of the invention, the device further comprises a data transmission device adapted to send data produced by the processing unit to a remote device.

In another embodiment of the invention, the method for acquiring and processing medical images of an ulcer comprises the steps of:
  providing a device according to any one of the above-listed provisions;
  positioning the device at a predefined distance from the ulcer, directing towards the latter the light sources and the image acquisition means;
  sequentially acquiring a plurality of images, equal to the number of light sources plus one;
  performing a step of combining and averaging the images, thereby obtaining an output image;
  applying a "cellular automaton" algorithm to the output image, thereby obtaining the contour of the ulcer and the contours of shadow areas around the ulcer, wherein each shadow area comprises a respective portion of ulcer extending beyond the edge of the respective contour and longitudinally with respect to a respective light source taken into consideration;
  calculating the depth of the ulcer on the basis of lengths of said shadow areas, as above specified, defined starting from the contours of the shadow areas and contour of the ulcer.

In another embodiment of the invention, the step of calculating the depth of the ulcer comprises the steps of:
  considering, for each shadow area, a point of origin O belonging to the contour of said shadow area and an end point F belonging to the contour of the ulcer, said points O and F having respective coordinates (o1, o2; f1, f2) in a Cartesian reference system;
  executing, for each shadow area, the following operations in order to calculate the depth of the ulcer in correspondence with each shadow area:

$$D = \sqrt{(o_1 - x_1)^2 + (o_2 - x_2)^2}$$

$$\gamma = \arctan\left(\frac{D}{h}\right)$$

$$L = \sqrt{(f_1 - o_1)^2 + (f_2 - o_2)^2}$$

$$p = L\frac{\cos(\gamma)}{\sin(\gamma)}$$

where D is the distance between a vertical light beam emitted by one of said sources having a respective position $(x_1, x_2, x_3)$ in said Cartesian reference system and the contour of the shadow area taken into account, $\gamma$ is the half-angle subtended by the light beam passing through the point O, and lastly p is the depth of the ulcer.

In another embodiment of the invention, the method further comprises the step of calculating the area of the ulcer as a function of the dimensions of a grid of photosensors associated with the image acquisition means and of a focal aperture angle of said image acquisition means in accordance with the following formulae:

$$\text{Area} = (2h)^2 \frac{\sin\left(\frac{\lambda_A}{2}\right)\sin\left(\frac{\lambda_B}{2}\right)}{\cos\left(\frac{\lambda_A}{2}\right)\cos\left(\frac{\lambda_B}{2}\right)}.$$

$$\text{Area}_{px} = \frac{\text{Area}}{px}.$$

$$\text{Area}_{TOT} = \text{Area}_{px} * N_{px}$$

where A and B are the dimensions of the rectangular sides of said grid of photosensors, $\text{Area}_{px}$ is the area of a single pixel of the output image, $N_{px}$ is the number of pixels contained in the contour of the ulcer.

In another embodiment of the invention, the step of acquiring a plurality of images comprises the steps of:
  progressively and sequentially turning on the light sources, synchronizing the on times with the acquisitions of the images by the image acquisition means in a manner such that each image can be acquired with a respective source switched on;
  acquiring, at the end of said progressive sequence, one last image with all sources simultaneously switched on.

In another embodiment of the invention, the images are acquired as colour images and the output image has three different colour shades.

BRIEF DESCRIPTION OF THE DRAWINGS

Further features and advantages of the invention will become apparent in the light of the following detailed description, provided by way of non-limiting example with reference to the annexed drawings, wherein.

DETAILED DESCRIPTION OF THE PREFERRED EMBODIMENTS

In brief, the present invention relates to a method for detecting and analyzing images of cutaneous ulcers by means of a device (which can be connected to a remote control device, such as a smartphone, a tablet, a PC, etc.) that allows the acquisition of images of patients' cutaneous lesions through a video camera or photo camera comprising at least three luminous devices. As an alternative, the device may be of the stand-alone type.

The data obtained after a subsequent step of analyzing such images can be sent to the doctor, who will then define the course of treatment of the patient (remote medicine, remote diagnosis).

The method for automatic detection of ulcers is based on an image acquisition and processing procedure. The method requires the use of a crown of light sources with characteristics known a priori (intensity, colour and heat of the emitted light and angle of the light rays emitted and incident on the wound), a video camera or photo camera, and a control unit (whether embedded or external) for synchronizing all such elements. The data thus obtained are then analyzed by means of a "cellular automaton" algorithm, which is per se known to those skilled in the art.

A "cellular automaton" (CA) algorithm is a particular type of algorithm based on the evolution of the internal states of a set of elements (called cells) arranged on a regular grid having finite dimensions (Wolfram, Stephen. Theory and applications of cellular automata. Vol. 1. Singapore: World Scientific, 1986).

The cells of the grid evolve at precise time intervals, changing their internal states according to external inputs and to the states of the neighbouring cells.

This class of algorithms draws inspiration from a number of evolutionary phenomena of various kinds that can be observed in nature. Assuming to associate the cells in question with the pixels that make up a digital image, circuits can be designed or algorithms can be implemented which can execute common image processing operations (Itoh, Makoto, and Leon O. Chua. "Memristor cellular automata and memristor discrete-time cellular neural networks" International Journal of Bifurcation and Chaos 19.11 (2009): 3605-3656) or which can recognize images (Secco, Jacopo, et al. "Memristor Cellular Automata through Belief Propagation Inspired Algorithm", IEEE ISOCC, Gyoungju, South Korea (2015)).

Documents CN1971619 and TW201231017 show how CA algorithms have been used for biomedical image analyses (especially Magnetic Resonance Images (MRI)).

Figure 1:
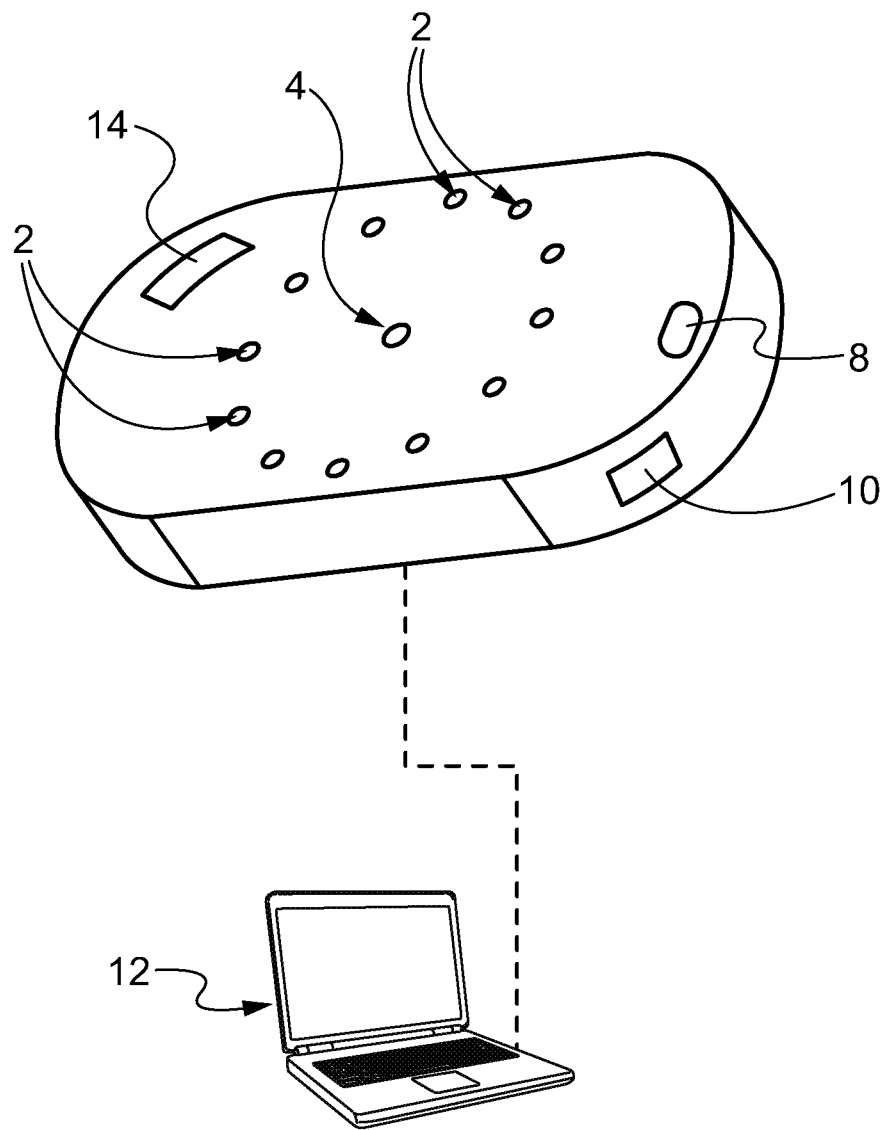
FIG. 1 is a perspective front view of a device for acquisition of medical images according to the present invention.

FIG. 1 shows a perspective front view of a device for acquisition of medical images 1 according to the present invention.

The device 1 comprises a crown of light sources 2, preferably white LEDs, a video camera or photo camera 4, preferably of the CMOS type, located at the center of the crown of light sources 2, removable memory means 6 (not represented in the Figure) adapted to store the images acquired by the video camera or photo camera 4, a distance sensing device 8, and a processing unit 10.

The distance sensing device 8 may be either analog or digital, acoustic or optical.

The light sources 2 are at least three and are arranged at regular intervals on the perimeter of a regular plane geometry (the circular crown) having a diameter of at least 10 cm.

As an alternative, the sources 2 are arranged on any closed regular plane geometry, the length of the minor axis being at least 10 cm.

The light sources 2 of the crown must be at least three, in that this is the minimum number required for completely irradiating a wound with overlapped beams.

Figure 2:
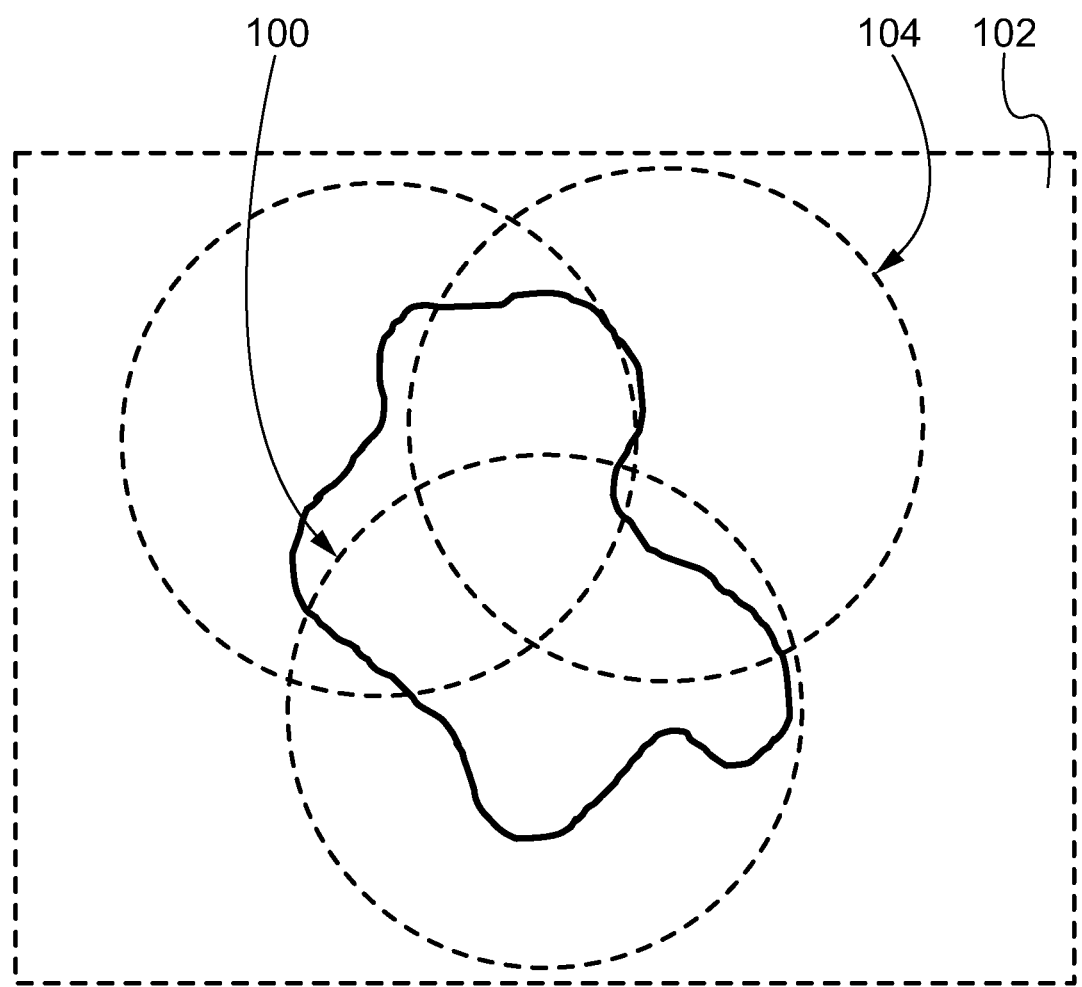
FIG. 2 shows a wound irradiated by light beams coming from the device of FIG. 1.

FIG. 2 shows a wound (ulcer) 100 of a skin portion 102 irradiated by light beams 104 coming from the light sources 2. Advantageously, the light beams 104 must cover the surface of the wound 100 in an overlapped fashion; in brief, the sum of the N-th fraction of the circumferences obtained with the illumination rays 104 must be greater than the area of the wound 100.

The light sources 2 have light intensity, colour and heat known a priori, and emit light rays or beams at predefined angles relative to the surface of the wound 100.

If the light sources 2 were fewer, they would have to be too close to each other to provide a shadow for each difference in level of the tissue, and this would not allow the whole surface of the pathological tissue to be covered. The diameter of the crown, preferably 10 cm, allows analyzing all possible wounds, since the average length of the major axis of a cutaneous ulcer is approximately 7 cm.

The processing unit 10 is connected to all of the above-mentioned components and is adapted to control the operation thereof in a per se known manner, so as to implement the method that will be described below. The processing unit 10 may be either a processor embedded in the device 1 or an external unit, e.g., associated with a remote device 12, such as a smartphone, a tablet, a PC, etc. The processing unit 10 allows synchronizing the operation of the other components through its own internal clock.

In a preferred variant of the invention, the device 1 further comprises a data transmission device 14 (GSM, 3G, WiFi, 4G, etc.) for sending data packets representative of the images to the remote device 12 or to another device (not shown in the drawings) available to a doctor.

Alternatively, the device 1 and the remote device 12 are connected through a USB cable.

Figure 3:
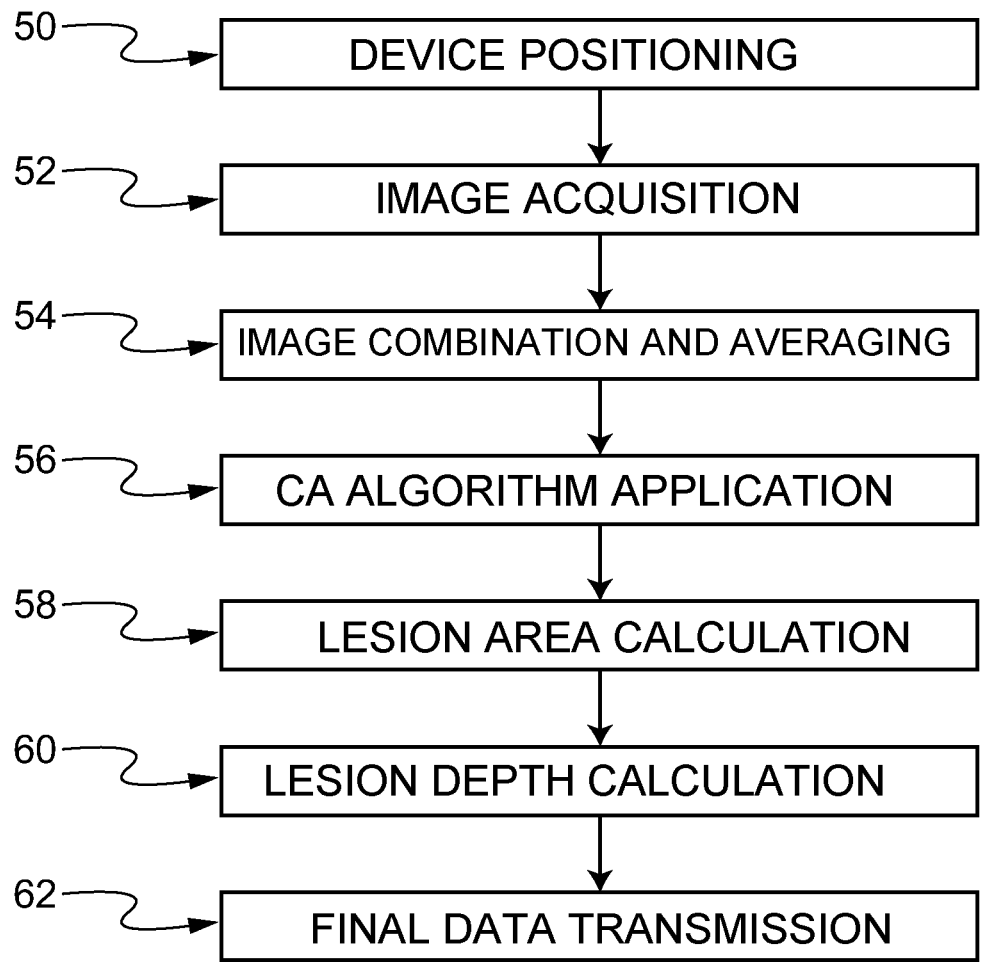
FIG. 3 is a diagram of the steps of the method for acquisition of medical images according to the present invention.

FIG. 3 shows a diagram of the steps of the method for analysis of medical images of ulcers according to the present invention.

In particular, the method is based on the acquisition, by the video camera or photo camera 4, of a plurality of images of the wound 100, said images being acquired with controlled and variable brightness, and on the subsequent processing of the images by the processing unit 10 through a "cellular automaton" algorithm.

The method for analysis of medical images according to the present invention starts at step 50 with the device 1 being positioned by a user at a predetermined distance h, e.g., ranging from 5 cm to 10 cm, from the wound 100, directing towards the latter the crown of light sources 2 and the video camera or photo camera 4.

The distance sensing device 8 measures, in a per se known manner, said distance h. If the measured distance h exceeds a predetermined threshold value, then the distance sensing device 8 will emit an audible signal to warn the patient that the device 1 has not been positioned correctly. Alternatively, the distance sensing device 8 may emit a luminous signal or a vibration.

As an alternative, the distance h is measured manually by the patient or by reading (in a manner per se known to those skilled in the art) the focusing of the video camera or photo camera 4 and of the optics connected thereto.

During the next step 52 the user points the video camera or photo camera 4 towards the wound 100 and starts, e.g., by pressing a start button of the video camera or photo camera 4, an image acquisition step. In particular, N+1 images of the wound 100 are acquired, where N is the number of light sources 2 of the crown.

The light sources 2 of the crown are turned on one at a time in sequence, synchronized with the image acquisitions made by the video camera or photo camera 4, so that one image is acquired with each light source 2 switched on. When a new source 2 is turned on, the one previously lit is turned off, so that the wound is illuminated by one source 2 at a time. At the end of the sequence, the video camera or photo camera 4 acquires one last image with all sources 2 switched on simultaneously.

The circular-crown arrangement of the light sources 2 allows irradiating the wound from different angles and generating shadows in the wound itself, so as to highlight any uneven parts of the wounded surface. Moreover, the crown formed by the light sources 2 having predefined characteristics ensures a precise illumination of the lesion 100, thus preventing result variability even in the long run.

Figure 4:
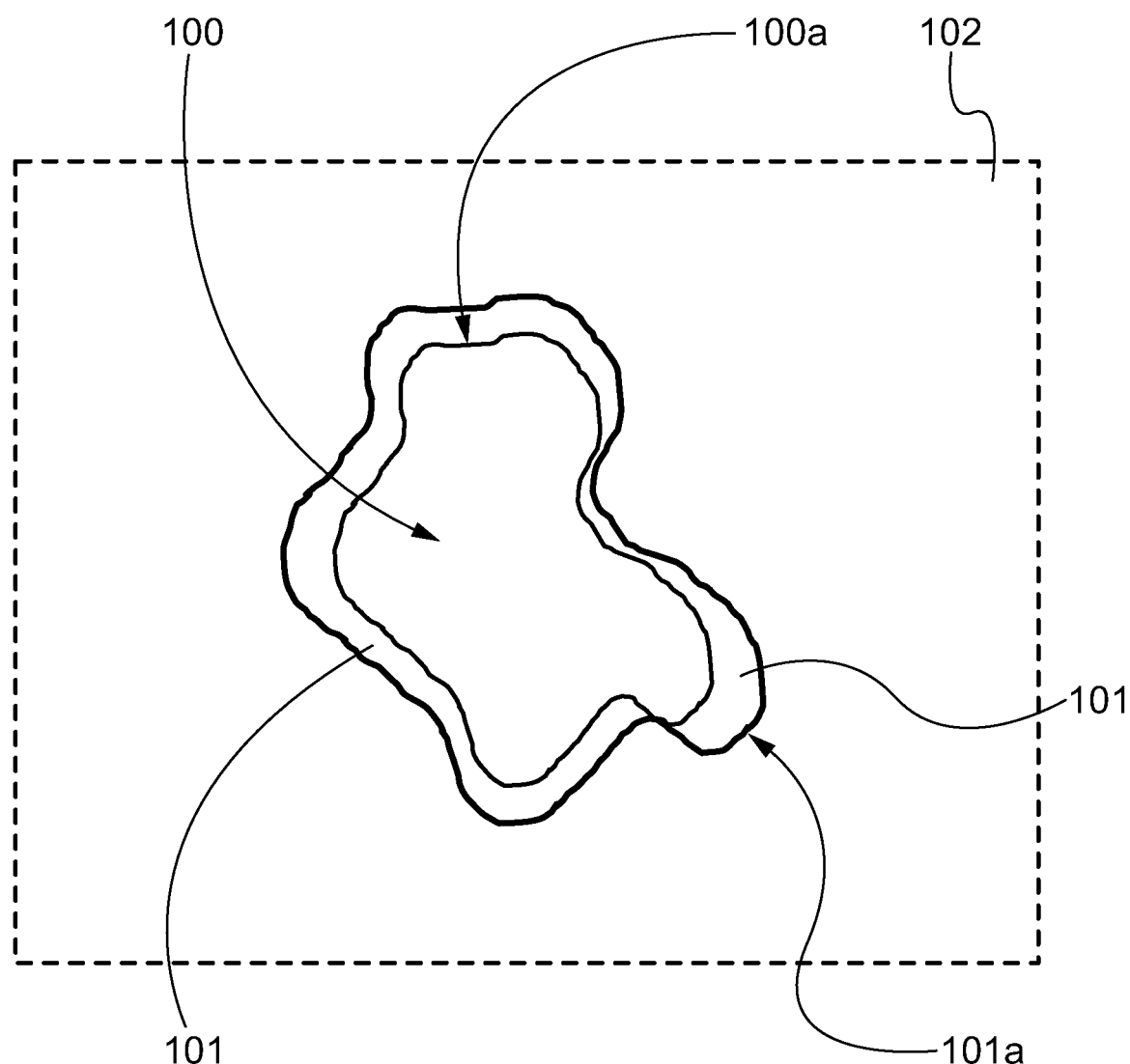
FIG. 4 shows the wound of FIG. 2, with the contours and shadows of the wound highlighted.

FIG. 4 shows the wound 100 of FIG. 2, highlighting the perimeter or contour 101a of the wound 100 and a series of shadow areas 101 having as a whole a perimeter or contour 100a.

By increasing the number of images of the ulcer 100 acquired from the same position, the signal-to-noise ratio can be reduced by combining and averaging the images by a factor equal to $\sqrt{K}$, where K is the number of acquired images. This will drastically reduce the motion artefacts caused by muscular tremor of the hand that is holding the device 1.

The images are acquired as colour images, i.e., RGB coded images.

In a subsequent step 54 said RGB image combining and averaging operation is carried out, thereby obtaining an output image of the wound 100 having three different colour shades.

At this point, an image processing step 56 is carried out by using a "cellular automaton" algorithm per se known to those skilled in the art, which is applied to the output image. The algorithm, executed by the processing unit 10, can segment the colours and decode them automatically, recognizing the contours 101a and 100a of the wound 100 and of its shadow areas 101, respectively.

The colours of the wounded region are decoded by generating a colour map and by utilizing the values of the output image obtained at step 54.

The number of photosensors of the video camera or photo camera 4 is equivalent to the number of pixels in the acquired images (hereafter referred to as px). The grid of photosensors of a CMOS video camera or photo camera has preferably a rectangular shape, and therefore has a major side A and a minor side B (see FIG. 5), but can also have a different shape, e.g., circular or square.

Figure 5:
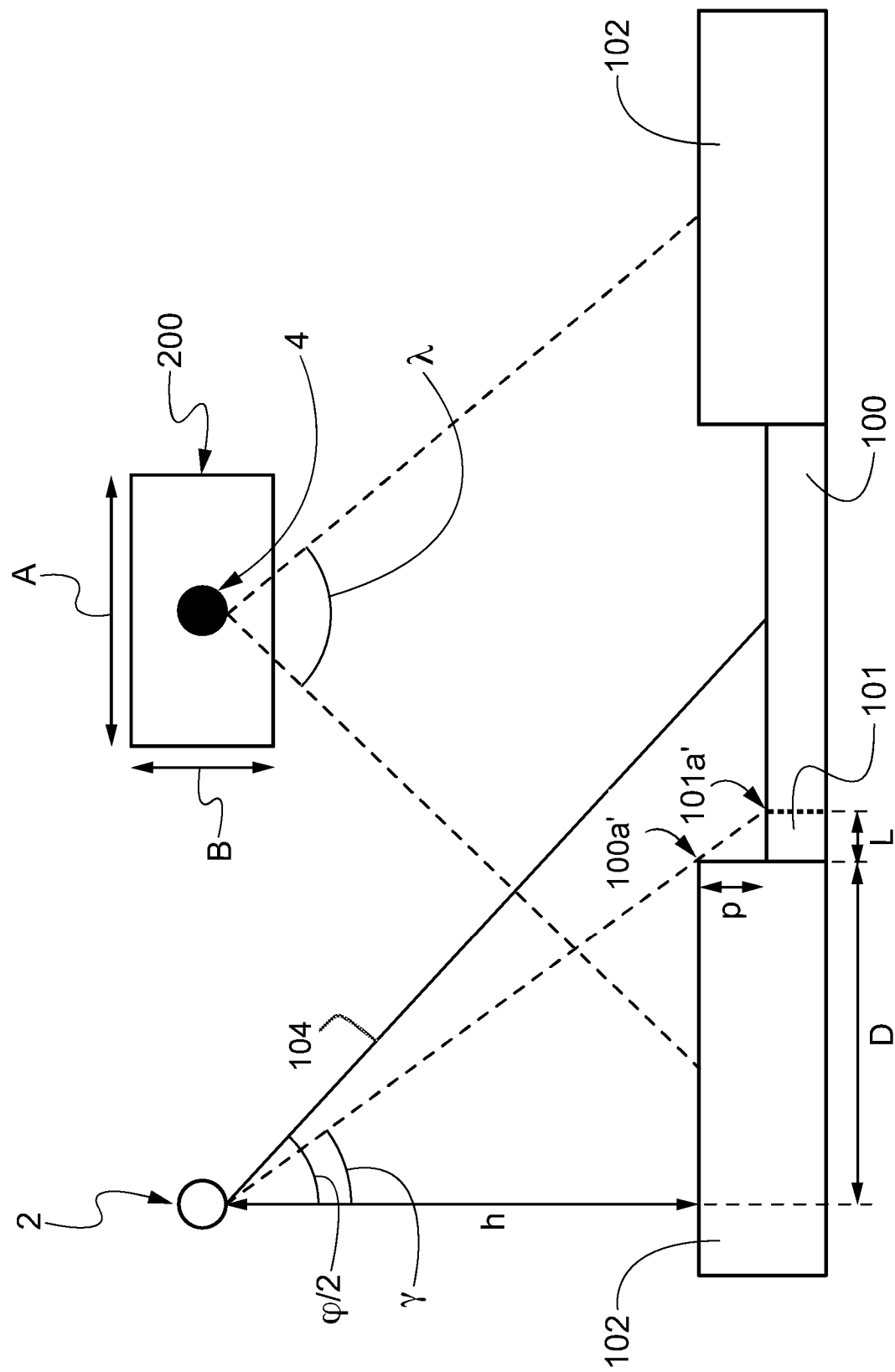
FIG. 5 is a sectional view of the device of FIG. 1 placed over a wound.

FIG. 5 is a sectional view of the device 1 positioned over the wound 100. It shows the video camera or photo camera 4 and one source light 2 of those comprised in the crown, which have respective positions X (x1, x2, x3) and Y (y1, y2, y3) in a Cartesian reference system.

The video camera or photo camera 4 has a focal aperture λ which is known a priori, and is associated, in a per se known manner, with a rectangular grid of photosensors 200 having a major side A and a minor side B, respectively. The light source 2 is placed at a distance h from the skin 102 with the wound 100, and emits a light beam 104 having an emission half-angle φ/2 directed towards the wound 100.

References 100a' and 101a' designate, respectively, two points of the contour 101a of the wound 100 and of the contour 100a of the shadow areas 101. Reference γ designates the half-angle subtended by the light beam 104 passing through the point 100a' of the contour 101a of the wound 100. Reference D designates the distance between the vertical ray emitted by the source 2 and the perimeter 101a of the ulcer 100, whereas L is the distance projected on the plane of the wound between the points 100a' and 101a' of the contours 101a and 100a of the wound 100 and of the shadow area 101.

With the data obtained at step 56 by means of the "cellular automaton" algorithm, during step 58 the processing unit 10 calculates the area of the lesion 100 by using the following formulae, where the subscripts A and B refer to the associated side of the grid of photosensors.

The focal area (Area) of the video camera or photo camera 4 is given by:

$$\text{Area} = (2h)^2 \frac{\sin\left(\frac{\lambda_A}{2}\right)\sin\left(\frac{\lambda_B}{2}\right)}{\cos\left(\frac{\lambda_A}{2}\right)\cos\left(\frac{\lambda_B}{2}\right)}.$$

The area of a single pixel ($\text{Area}_{px}$) is given by:

$$\text{Area}_{px} = \frac{\text{Area}}{px}.$$

The number of pixels $N_{px}$ contained within the border 101a multiplied by $\text{Area}_{px}$ gives as a result the area of the lesion 100, according to the following formula:

$$\text{Area}_{TOT} = \text{Area}_{px} * N_{px}$$

Subsequently, at step 60, for each shadow area 101 the processing unit 10 calculates the length L of the shadow starting from its point of origin, in order to obtain the depth p of the wound 100.

For a given shadow area 101 generated by a single light source 2, a point of origin O ($o_1$, $o_2$) corresponding, for example, to the point 100a' and an end point F ($f_1$, $f_2$) corresponding to the point 101a' are considered (O and F are therefore only known in the two-dimensional plane when an image is acquired and their distance represents the length L of the shadow area). During this step 60 the following operations are thus carried out in order to calculate the depth p of the wound 100:

$$D = \sqrt{(o_1 - x_1)^2 + (o_2 - x_2)^2}$$

$$\gamma = \arctan\left(\frac{D}{h}\right)$$

$$L = \sqrt{(f_1 - o_1)^2 + (f_2 - o_2)^2}$$

$$p = L\frac{\cos(\gamma)}{\sin(\gamma)}$$

Step 60 is repeated for each image within the contour 101a, thereby obtaining a plurality of depth values p representative of the depth of the wound 100 along its whole perimeter 101a. Finally, during step 62, the final data about the wound 100 (in particular, its depth and area) are outputted to the processing unit 10.

Advantageously, said final data are either stored into the memory means 10 of the device 1 or sent to the doctor through the data transmission device 14.

Therefore, the device 1 of the present invention has the following innovative features:
full control over the brightness of the image, resulting in less external luminous noise, which often generates artefacts in the processed image;
it can be used for remote diagnoses, since it includes a data transmission module;

a multi-image packet is used for automatically detecting the wound and for calculating the depth of the ulcer, wherein each image is taken with monochromatic light having known intensity and colour, but coming from a spatially variable source. This allows the image processing algorithm to comprehend the three-dimensionality of the wound through the variations in the shadows generated by the indentation at the border of the ulcer;

this is the first remote medical device for this purpose that must not be used exclusively by skilled or previously trained personnel. The use of this device is completely entrusted to the patient, and this improves the portability thereof. As described above, it also allows the doctor, downstream of the use of the device, to perform accurate and effective remote diagnoses and follow-ups of the patient's conditions, while fully conforming to the latter's needs (walking difficulty, old age, clinical conditions that prevent movement, etc.).

it has low development and production costs because it utilizes simple technologies.

Of course, without prejudice to the principle of the invention, the embodiments and the implementation details may be extensively varied from those described and illustrated herein by way of non-limiting example, without however departing from the protection scope of the present invention as set out in the appended claims.

The invention claimed is:

1. A device for acquisition of medical images of an ulcer, comprising:
   a plurality of light sources arranged on a perimeter of a plane geometry, and adapted to illuminate the ulcer by means of respective light beams covering a surface of the ulcer in a partially overlapped fashion, such that at least one area of said surface of said ulcer is illuminated by all of said plurality of light sources, and that at least one area of said surface of said ulcer is illuminated by only a subset of the plurality of light sources, wherein during use,
   an arrangement of said plurality of light sources is adapted to irradiate the ulcer from different angles to generate shadow areas around an edge of the ulcer due to unevenness of said surface of said ulcer compared to normal skin that surrounds the ulcer, and
   said at least one area that is irradiated by only said subset of said plurality of light sources includes a portion of said edge of said ulcer, such that at least one shadow area among said shadow areas around said portion of said edge is generated;
   image acquisition means placed within said perimeter of the light sources and adapted to acquire medical images of said illuminated ulcer; and
   a processing unit adapted to:
   identify, for each single shadow area among said shadow areas generated by each single light source among said plurality of light sources, a point of origin O belonging to a contour of the ulcer and an end point F belonging to the contour of said single shadow area, said points O and F having respective coordinates in a Cartesian reference system, and a length (L) of the contour between points O having coordinates ($o_1$, $o_2$) and F having coordinates ($f_1$, $f_2$) representing a length of said shadow area;
   calculate a depth of the ulcer in correspondence with each shadow area based on equations below:

$$D = \sqrt{(o_1 - x_1)^2 + (o_2 - x_2)^2}$$
$$\gamma = \arctan\left(\frac{D}{h}\right)$$
$$L = \sqrt{(f_1 - o_1)^2 + (f_2 - o_2)^2}$$
$$p = L\frac{\cos(\gamma)}{\sin(\gamma)}$$

where D is a distance between a vertical light beam emitted by one of said plurality of light sources having a respective position ($x_1$, $x_2$, $x_3$) in said Cartesian reference system and the contour of the shadow area taken into account, h is a distance between the device and the ulcer, y is a half-angle subtended by said light beam passing through the point O, and p is the depth of the ulcer.

2. The device according to claim 1, the processing unit further comprising a processor connected to said sources and image acquisition means, and adapted to control both the illumination of the ulcer and the acquisition of the images.

3. The device according to claim 2, further comprising a data transmission device adapted to send data produced by the processor to a remote device.

4. The device according to claim 1, further comprising a distance sensor adapted to measure the distance (h) between the device and the ulcer and to send an alarm signal if said distance exceeds a predefined threshold value.

5. The device according to claim 4, wherein the distance sensor is either analog or digital, and the distance sensing device is acoustic or optical.

6. The device according to claim 1, wherein the light sources are at least three.

7. The device according to claim 1, wherein the light sources are white LEDs.

8. The device according to claim 1, further comprising removable memory means adapted to store the images acquired by the image acquisition means.

9. The device according to claim 1, wherein the plane geometry has a minor axis of at least 10 cm.

10. A method for acquiring and processing medical images of an ulcer, comprising the steps of:
    positioning a device at a predefined distance from the ulcer, the device comprising a plurality of light sources arranged on a perimeter of a plane geometry, an image acquisition means, and a processing unit;
    irradiating the ulcer by said plurality of light sources from different angles to generate shadow areas within a surface of the ulcer;
    sequentially acquiring a plurality of images by said image acquisition means when the ulcer is being irradiated by at least one of the plurality of light sources, the plurality of images being equal to the number of light sources plus one;
    combining and averaging said plurality of images by said processing unit, thereby obtaining an output image;
    applying a cellular automaton algorithm to said output image by said processing unit, thereby obtaining a contour of the ulcer and contours of the shadow areas within the surface of the ulcer, wherein each shadow area comprises a respective portion of the ulcer extending beyond an edge of the respective contour of the ulcer;
    calculating, by said processing unit, a depth of the ulcer on the basis of lengths of said shadow areas defined starting from said contour of the ulcer and contours of the shadow areas, wherein the step of calculating the depth of the ulcer comprises the steps of:
identify, for each single shadow area among said shadow areas generated by each single light source among said plurality of light sources, a point of origin O belonging to a contour of the ulcer and an end point F belonging to the contour of said single shadow area, said points O and F having respective coordinates in a Cartesian reference system, and a length (L) of the contour between points O having coordinates ($o_1$, $o_2$) and F having coordinates ($f_1$, $f_2$) representing a length of said shadow area;
executing, for each image, the following operations in order to calculate the depth of the ulcer in correspondence with each shadow area:

$$D = \sqrt{(o_1 - x_1)^2 + (o_2 - x_2)^2}$$

$$\gamma = \arctan\left(\frac{D}{h}\right)$$

$$L = \sqrt{(f_1 - o_1)^2 + (f_2 - o_2)^2}$$

$$p = L\frac{\cos(\gamma)}{\sin(\gamma)}$$

where D is a distance between a vertical light beam emitted by one of said plurality of light sources having a respective position ($x_1$, $x_2$, $x_3$) in said Cartesian reference system and the contour of the shadow area taken into account, h is a distance between the device and the ulcer, y is a half-angle subtended by said light beam passing through the point O, and p is the depth of the ulcer.

11. The method according to claim 10, wherein the step of acquiring a plurality of images comprises the steps of:
progressively and sequentially turning on the light sources, synchronizing the on times with the acquisitions of the images by the image acquisition means in a manner such that each image can be acquired with a respective source switched on;
acquiring, at the end of said progressive sequence, one last image with all sources simultaneously switched on.

12. The method according to claim 10, further comprising the step of calculating the area of the ulcer as a function of the dimensions of a grid of photosensors associated with the image acquisition means and of a focal aperture angle ($\lambda$) of said image acquisition means in accordance with the following formulae:

$$\text{Area} = (2h)^2 \frac{\sin\left(\frac{\lambda_A}{2}\right)\sin\left(\frac{\lambda_B}{2}\right)}{\cos\left(\frac{\lambda_A}{2}\right)\cos\left(\frac{\lambda_B}{2}\right)}.$$

$$\text{Area}_{px} = \frac{\text{Area}}{px}.$$

$$\text{Area}_{TOT} = \text{Area}_{px} * N_{px}$$

where A and B are the dimensions of the rectangular sides of said grid of photosensors, $\underline{\text{Area}}_{px}$ is the area of a single pixel of the output image, $N_{px}$ is the number of pixels contained in the contour of the ulcer.

13. The method according to claim 12, wherein said images are acquired as colour images and the output image has three different colour shades.

* * * * *